(12) United States Patent
Bettenworth et al.

(10) Patent No.: US 9,156,881 B2
(45) Date of Patent: Oct. 13, 2015

(54) TRIPEPTIDE KDPT FOR ANTIAPOPTOTIC TREATMENT

(71) Applicants: Dominik Bettenworth, Cosfeld (DE); Markus Boehm, Muenster (DE); Andreas Luegering, Muenster (DE)

(72) Inventors: Dominik Bettenworth, Cosfeld (DE); Markus Boehm, Muenster (DE); Andreas Luegering, Muenster (DE)

(73) Assignee: WESTFAELISCHE WILHELMS-UNIVERSITAET MUENSTER, Muenster (DE)

( * ) Notice: Subject to any disclaimer, the term of this patent is extended or adjusted under 35 U.S.C. 154(b) by 0 days.

(21) Appl. No.: 14/344,398

(22) PCT Filed: Sep. 24, 2012

(86) PCT No.: PCT/EP2012/068755
§ 371 (c)(1),
(2) Date: Mar. 12, 2014

(87) PCT Pub. No.: WO2013/041719
PCT Pub. Date: Mar. 28, 2013

(65) Prior Publication Data
US 2014/0323394 A1 Oct. 30, 2014

(30) Foreign Application Priority Data
Sep. 23, 2011 (EP) .................................. 11182561

(51) Int. Cl.
| | | |
|---|---|---|
| *A61K 38/06* | (2006.01) | |
| *A61K 38/34* | (2006.01) | |
| *C07K 5/08* | (2006.01) | |
| *C07K 5/09* | (2006.01) | |

(52) U.S. Cl.
CPC ............... *C07K 5/0815* (2013.01); *A61K 38/06* (2013.01); *A61K 38/34* (2013.01)

(58) Field of Classification Search
CPC ....... A61K 38/06; A61K 38/34; C07K 5/0815
USPC .......................... 514/17.8, 18.9, 3.8; 530/331
See application file for complete search history.

(56) References Cited

U.S. PATENT DOCUMENTS

| | | | |
|---|---|---|---|
| 8,003,608 B2 * | 8/2011 | Luger | ........................ 514/10.7 |
| 2004/0077552 A1 | 4/2004 | Luger | |
| 2010/0286056 A1 * | 11/2010 | Bohm | .......................... 514/18.8 |
| 2012/0045462 A1 * | 2/2012 | Luger | ....................... 424/184.1 |

FOREIGN PATENT DOCUMENTS

WO   WO 2009/065857   5/2009

OTHER PUBLICATIONS

Favaloro et al, "Role of Apoptosis in disease," Aging, 2012, 4(5): 330-349.*
Solary et al, "The role of apoptosis in the pathogenesis and treatment of diseases," European Respiratory Journal, 1996, 9: 1293-1305.*
Alzheimer's disease from Merck manual, pp. 1-17. accessed Jul. 29, 2009.*
Mattson MP, "Pathways towards and away from Alzheimer's disease," Nature, 2004, 430: 631-639.*
HIV from Merck Manual, pp. 1-25. Accessed Oct. 8, 2014.*
PCT Search Report for International Application No. PCT/EP2012/068755; mailed on Dec. 3, 2012.
Bettenworth, D., et al., (2009) *The Melanocortin-Derived Tripeptide K(D)PT Ameliorates the Course of Murine Colitis*, Gastroenterlogy (AGA Abstract #M1649) 136: A-402.
Brozka, T., et al., (2008) α-*Melanocyte-Stimulating Hormone and Related Tripeptides: Biochemistry, Antiinflammatory and Protective Effects in Vitro and in Vivo, and Future Perspectives for the Treatment of Immune-Mediated Inflammatory Diseases*, Endocrine Reviews 29: 581-602.
Meyer, N., et al., (2010) *IL-32 is expressed by human primary keratinocytes and modulates keratinocyte apoptosis in atopic dermatitis*, J Allergy Clin Immunol 125: 858-865.
Ruiz-Argüelles, A., et al., (2007) *Apoptosis of melanocytes in vitiligo results from antibody penetration*, Journal of Autoimmunity 29: 281-286.
Trautmann, A., et al., (2005) *Apoptosis and Loss of Adhesion of Bronchial Epithelial Cells in Asthma*, Int Arch Allergy Immunol 138: 142-150.

* cited by examiner

*Primary Examiner* — Julie Ha
(74) *Attorney, Agent, or Firm* — Kagan Binder, PLLC

(57) ABSTRACT

The present invention is related to the tripeptide (l)Lys-(d)Pro-(l)Thr (KdPT) or pharmaceutically acceptable salts thereof for therapeutic, prophylactic therapeutic or cosmetic treatment of a disease with increased apoptosis, wherein the treatment has an anti-apoptotic effect. The present invention is also related to the use of KdPT or pharmaceutically acceptable salts thereof for the manufacture of a pharmaceutical or cosmetic composition for an anti-apoptotic treatment of disorders that are related with increased apoptosis.

10 Claims, 2 Drawing Sheets

TRIPEPTIDE KDPT FOR ANTIAPOPTOTIC TREATMENT

The present invention is related to the tripeptide (l)Lys-(d)Pro-(l)Thr (KdPT) or pharmaceutically acceptable salts thereof for therapeutic, prophylactic therapeutic or cosmetic treatment of a disease with increased apoptosis, wherein the treatment has an anti-apoptotic effect. The present invention is also related to the use of KdPT or pharmaceutically acceptable salts thereof for the manufacture of a pharmaceutical or cosmetic composition for an anti-apoptotic treatment of disorders that are related with increased apoptosis.

In multicellular organisms, homeostasis is maintained through a balance between cell proliferation and cell death. Although much is known about the control of cell proliferation, less is known about the control of cell death. Physiologic cell death occurs primarily through an evolutionarily conserved form of cell suicide termed apoptosis.

Apoptosis, in contrast to necrosis, is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound-vesicles (apoptotic bodies) which contain ribosomes, morphologically intact mitochondria and nuclear material. In vivo, these apoptotic bodies are rapidly recognized and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has also been termed "secondary necrosis". Maintaining the balance between cell proliferation and cell death is of pivotal importance to homeostasis of tissues and organs. In general terms, imbalances that favor cell proliferation lead to neoplasms, while excess cell death triggers inflammatory responses. Programmed cell death responses are typically classified as apoptosis (type I), autophagy (type II), or necrosis (type III). Apoptosis is a physiological process that eliminates unwanted, damaged, or virus-infected cells in a way that does not evoke an inflammatory response. Upon binding by their cognate ligands, cell surface death receptors (DRs), CD95 (Fas/APO-1), TNFR1, DR3, DR4, and DR55 form homotrimers that recruit death domain (DD) containing molecules, such as FADD (Fas-associated death domain)6 or TRADD (tumor necrosis factor [TNF]-receptor associated death domain), through the interaction with their intracellular DDs. This initiates the extrinsic pathway of apoptosis, so-termed because it is activated by extracellular signals. Following the recruitment of FADD to DRs, its death effector domain binds to caspase-8, an enzyme that serves as the initiator of apoptosis through dimerization and self-cleavage followed by activation of downstream effector caspases, such as caspase-3. In contrast, the intrinsic pathway of apoptosis is triggered by an intracellular death signal involving mitochondrial dysfunction and resulting in formation of the apoptosome, which contains Apaf-1, cytochrome c, procaspase-9, and ATP/dATP.9 Conversion of procaspase-9 to the active form allows caspase-9 to cleave, and thereby activate, pro-caspase-3, the most important executioner caspase. Knockout mouse studies have shown that both caspase-3 and the related caspase-7 are critical to the intrinsic apoptosis pathway (Lina Chen, PhD,* et al. Inflamm Bowel Dis Volume 16, Number 6, June 2010).

Cell apoptosis can be influenced by a wide variety of regulatory stimuli. Recent evidence suggests that alterations in cell survival contribute to the pathogenesis of a number of human diseases, including cancer, viral infections, autoimmune diseases, neurodegenerative disorders, and AIDS (acquired immunodeficiency syndrome). Treatments designed to specifically alter the apoptotic threshold may have the potential to change the natural progression of some of these diseases (Thompson, Craig B., Science, Volume 267, Issue 5203, pp. 1456-146). Several diseases are characterized by the accumulation of cells due to an increased cell survival which are diseases associated with the inhibition of apoptosis, such as e.g. cancer. A second group of diseases are characterized by an increased apoptosis e.g. AIDS, neurodegenerative disorders such as Alzheimer's disease, Parkinson's disease, or myocardial infarction and stroke, and also toxin-induced liver disease. Excessive cell death can result from acquired or genetic conditions that enhance the accumulation of signals that induce apoptosis or that decrease the threshold at which such events induce apoptosis. Although increased apoptotic cell death has been observed in many diseases, in most degenerative disorders an underlying defect in cell death control has-not been defined.

First studies have been published on cellular changes including the observation of apoptotic events during colitis. Although CD95 could be excluded as a causative agent for the apoptosis observed in the intestinal epithelial cells in inflammatory bowel diseases, the mechanism of this cell loss remains to be determined. Thus, it is not known yet what function of autophagy, cell survival, or cell death, is dysregulated and results in cell loss. In summary, the mechanisms that underlie the loss of intestinal epithelial cells still remain elusive (Lina Chen, PhD,* et al. Inflamm Bowel Dis Volume 16, Number 6, June 2010).

Several types of inhibitors of apoptosis are known in the prior art. Physiologic inhibitors comprise e.g. growth factors, extracellular matrix, CD40 ligand, neutral amino acids, zinc, estrogen, and andogens. Viral genes that are known to inhibit apoptosis are e.g. Adenovirus E1B, Cowpox virus crmA, Epstein-Barr virus BHRF1, LMP-1 and the Herpesvirus gamma1 34.5. Among the pharmacological agents that inhibit apoptosis there are calpain inhibitors, cysteine protease inhibitors and tumor promoters PMA, phenobarbital and alpha-Hexachlorocyclohexane (Thompson, Craig B., Science, Volume 267, Issue 5203, pp. 1456-146).

As these apoptosis inhibitors are pathogenic, these types of inhibitors of apoptosis are not suitable in order to treat or cure disorders that are related to an increased apoptosis.

In the context of controlled medical application of an apoptosis inhibitor, one type of the melanocyte-stimulating hormone belonging to a group called the melanocortins, namely α-MSH, was described in the prior art. α-MSH is a cleavage product of a large precursor peptide called pro-opiomelanocortin (POMC). α-MSH is the most important melanocortin for pigmentation. α-MSH was shown to act as a suppressor of apoptosis in nonneuronal cells and pretreatment of α-MSH may have some inhibitory effect on cyclosporine-A (CsA) induced tubular cell apoptosis (Sang Kyung Jo et al., J Korean Med Sci 2001; 16: 603-9). Also α-MSH analogs have been suggested as a novel melanoma preventive strategy. E.g. the peptides Ac-His-D-Phe-Arg-Trp-NH$_2$, n-pentadecanoyl- and 4-phenylbutyryl-His-D-Phe-Arg-Trp-NH$_2$ were assessed for their in vitro capacity to stimulate tyrosinase (thus increasing melanogenesis), to reduce UVB-induced apoptosis and release of H₂O₂, and to enhance removal of cyclopyrimidine dimers after UVB exposure. The latter two peptides were more potent than the former or α-MSH at 1 nM (Brzoska et al., Endocr. Rev 2008, 29:581-602). Despite first results relating to a controlled treatment in order to reduce pathogenic apoptotic cell death, little is known about the mechanism that lead to the increase of a cell's resistance to undergo apoptosis although such a knowledge would be of benefit in e.g. treating degenerative disorders.

The tripeptide KdPT belongs to a group of tripeptides derived from α-MSH, which is one type of melanocyte-stimulating hormone belonging to a group called the melanocortins. α-MSH is a cleavage product of a large precursor peptide called pro-opiomelanocortin (POMC). Alpha-MSH is the most important melanocortin for pigmentation. Several studies indicate that the immunomodulating and antiinflammatory effects of α-MSH are also mediated by last three C-terminal amino acids of α-MSH, a-MSH(11-13): Lys-Pro-Val. For example, Catania et al could demonstrate that the application of a-MSH(11-13) was able to induce said effects (Catania and Lipton, 1993, Endocr. Rev. 14, 564-576; Bhardvaj et al., 1996, J. Immunol. 156, 2517-2521). WO 88/00833 describes the use of the tripeptide Lys-Pro-Val for the production of a medicament in order to treat inflammations. The C-terminal tripeptide was also proposed as a medicament against alopecia (FR2733421). Furthermore, the therapeutic potential of the melanocortin-derived tripeptide alpha-MSH (11-13) (KPV) was investigated e.g. in 2 models of intestinal inflammation. Melanocortin-derived tripeptide KPV has anti-inflammatory potential in murine models of inflammatory bowel disease (Klaus Kannengiesser, et al. Inflamm Bowel Dis 14(3):324-31 (2008) PMID 18092346). The most preferred tripeptide in the context with antiinflammatory effects particularly for treating inflammatory bowel disease was described to be KdPT. The tripeptide KdPT is a melanocortin-derived tripeptide comprising the amino acids H-Lysine-D-Prolin and Threonine. Furthermore it has been described that KdPT suppresses IL-1(beta)-mediated cytokine expression and signaling in human sebocytes (J. of Immunology, 2010, http://www.jimmunol.org/cgi/content/full/jimmunol.0902298/DC1). Furthermore, KdPT as an anti-inflammatory small molecule was investigated in-vivo and in vitro. Intestinal inflammation was studied after oral administration of dextran sodium sulfate and in IL-10 gene-deficient mice. The effects of KdPT on key colonic epithelial cell functions were studied in vitro and in vivo by evaluating proliferation, wound healing, transepithelial resistance, and expression of tight junction proteins (Bettenworth at al. Americ. J. Path., Vol. 179, No.3, Sept 2011). Melanin assays were performed to determine the melanotropic effects of KdPT. KdPT-treated animals showed markedly reduced severity of inflammation in both colitis models. In colonic epithelial cells, KdPT increased proliferation, accelerated closure of wounds, and improved transepithelial electrical resistance after stimulation with interferon-γ/tumor necrosis factor-α. Moreover, treatment with KdPT also prevented the loss of tight junction protein expression and improved barrier function in vivo. KdPT acted independently of IL-1 receptor type I in vivo and did not affect melanogenesis in vitro. KdPT is capable of attenuating the course of experimental colitis in different models and maintains epithelial cell function. Furthermore, KdPT does not induce pigmentation, emphasizing the potential of this small molecule for the future treatment of inflammatory bowel disease. (Bettenworth D, at al., Am J Pathol. 2011 Sep;179(3):1230-42. Epub 2011 Jul 8).

In the context of treating apoptotic occurrences regarding the reduction of UVB-induced apoptosis and release of H₂O₂, and to enhance removal of cyclopyrimidine dimers after UVB exposure, the petids peptides Ac-His-D-Phe-Arg-Trp-NH₂, n-pentadecanoyl- and 4-phenylbutyryl-His-D-Phe-Arg-Trp-NH₂ were discussed in the literature, whereas the tripeptide KdPT was described to act as an anti-inflammatory substance, particularly in the context of inflammatory bowel disease. (Bettenworth D, et al., Am J Pathol. 2011 Sep;179 (3):1230-42. Epub 2011 Jul 8).

It has now surprisingly been found by the inventors, that the tripeptide KPdT or pharmaceutically acceptable salts thereof shows a general antiapoptotic effect and is thus a suitable substance in order to treat various disorders or undesired cosmetical occurences which are accompanied with increased apoptosis.

The present invention is thus related to the use of the tripeptide lysine-proline-threonine with the configuration (l)Lys-(d)Pro-(l)Thr (KdPT) or pharmaceutically acceptable salts thereof for therapeutic, prophylactic therapeutic or cosmetic treatment of a disease with increased apoptosis, wherein the treatment has an anti-apoptotic effect.

The amino acids constituting the tripeptides of the invention, KdPT show the following stereoisomeric configuration: Lysine is an L-enantiomer, proline is configurated as D-enantiomer and threonine is configurated as L-enantiomer.

The tripeptide KdPT or pharmaceutically acceptable salts thereof used according to the invention may be chemically modified. Generally, all kind of modifications of KdPT or pharmaceutically acceptable salts thereof are comprised by the present invention as long as they do not inhibit the anti-apoptotic effect of the peptid or salt respectively. E.g. modifications at the N terminus and/or at the C terminus of the tripeptide might be performed, for example by an acyl group, preferably an acetyl group at the N terminus and/or an amidation or esterification of the C terminus.

Generally the N-terminus is located at the amino acid lysine (abbreviated K) and the C-terminus at the amino acid threonine (abbreviated T). Accordingly, one preferred embodiment of the present invention is the use of KdPT or pharmaceutically acceptable salts thereof whereas KdPT is configurated $^N$KdPT$^C$, whereas the supercripted letters "N" and "C" stand for "N-terminus" and "C-terminus", respectively.

Further protective groups known per se are likewise possible. The modifications may also affect the amino group in the side chain of lysine or the hydroxyl group of threonine. Other modifications are also conceivable on the side of the NH₂ group, e.g. extension by a glycine, and further amino acid residues up to the length of α-MSH.

Other chemical modifications of the compounds of the invention such as alkylation (e. g., methylation, propylation, butylation), arylation, etherification and esterification may be possible and are also envisaged. It is preferred that the mentioned modifications do not significantly alter the advantageous capabilities of the compounds of the invention as described herein, i.e. the chemically modified compounds of the invention have capabilities which are comparable with the capabilities of the compounds which were evaluated in the appended examples. "Comparable" is explained herein below.

It may be necessary, for reasons of resistance to degradation, to employ a protected form of the compounds of the invention. The nature of the protecting group must obviously be a biologically compatible form. Many biologically compatible protective groups are suitable, such as, for example, those provided by acylation or acetylation of the amino-terminal end or amidation of the carboxy-terminal end.

Thus, the invention also features the compounds of the invention in a protected or unprotected form. Protective groups based either on acylation or acetylation of the amino-terminal end or on amidation of the carboxy-terminal end or, alternatively, on both, are the preferred.

Further protective groups known per se are likewise possible. The modifications may also affect the amino group in the side chains of the amino acids. As stated above, it is preferred that these modifications do not significantly alter the advantageous capabilities of the compounds of the invention as described herein.

In a more preferred embodiment of the invention the above mentioned tripeptides are amidated at the C-terminus; for instance compound pGlu-His-Pro is amidated at the C-terminus.

Thus, a further embodiment of the present invention is the use of the tripeptide KdPT or pharmaceutically acceptable salts thereof which are chemically modified.

For the purpose of the invention the active compound as defined above also includes the pharmaceutically or cosmetically acceptable salt(s) thereof. The phrase "pharmaceutically or cosmetically acceptable salt(s)", as used herein, means those salts of compounds of the invention that are safe and effective for the desired administration form. Pharmaceutically or cosmetically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The use of salt formation as a means of varying the properties of pharmaceutical compounds is well known and well documented. Salt formation can be used to increase or decrease solubility, to improve stability or toxicity and to reduce hygroscopicity of a drug product. There are a wide range of chemically diverse acids and bases, with a range of pKa values, molecular weights, solubilities and other properties, used for this purpose. Of course, any counterions used in pharmaceuticals must be considered safe, and several lists of pharmaceutically approved counterions exist, which vary depending on the source. Approved salt formers can e.g. be found in the Handbook of Pharmaceutical Salts (Stahl P H, Wermuth C G, editors. 2002. Handbook of pharmaceutical salts: Properties, selection and use. Weinheim/Zurich: Wiley-VCH/VHCA.). Thus, the present invention also comprises the use of pharmaceutically acceptable salts of KdPT.

In the present invention the term "anti-apoptotic effect" comprises any measurable decrease of undesired or pathogenic apoptosis rate. In the present invention the term "increased apoptosis" means an increased apoptosis rate compared to the average apoptosis rate in a correspondent non-pathogenic condition. A disease with increased apoptosis means in general that the disease is characterized by (is attended by) an abnormal rate of apoptosis in tissues, body fluids and/or organs. This can be determined e.g., by flow-cytometrie. The term "increased rate of apoptosis" as used herein means that the rate of apoptotic cells by e.g. measured by flow-cytometrie is measurable higher as compared with a normal/natural state of a comparable control-cell/subject. It has to be understood that in the context of the present invention, the terms increased apoptosis and and increased rate of apoptosis are used interchangeably. The term "normal/natural state of a comparable control-cell/subject" means the rate of apoptosis in a control-target cells, tissue, body fluid and/or organ which are/is preferably of the same nature as the test-cells target tissue, body fluid and/or organ but which are/is derived from a different source. "A different source" includes e.g. a cell/tissue sample obtained from a healthy subject which does not suffer from a disease which is associated with increased apoptosis or a cell/tissue sample obtained from a distinct joint of the same subject wherein said different joint appears to be free from associated symptoms of a disease which is associated with increased apoptosis.

Apoptotic cell death can be distinguished from necrotic cell death. Necrotic cell death is a pathologic form of cell death resulting from acute cellular injury, which is typified by rapid cell swelling and lysis. In contrast, apoptotic cell death is characterized by controlled autodigestion of the cell. Cells appear to initiate their own apoptotic death through the activation of endogenous proteases. This results in cytoskeletal disruption, cell shrinkage, and membrane blebbing. Apoptosis also involves characteristic changes within the nucleus. The nucleus undergoes condensation as endonucleases are activated and begin to degarde nuclear DNA. In many cell types, DNA is degraded into DNA fragments the size of oligonucleosomes.

Increased apoptosis can be measured by any suitable method known in the art. Examples of suitable methods comprise radioactive or non-radioactive DNA fragmentation assays such as DNA staining, Flow-Cytometrie and dual laser flow-cytometrie, JAM Test, Alkaline Elution Analysis, DNA ladder Assay, nucleosome quantification (sell death detection ELISA), radioactive DNA ladder assay, protease activity assay such as caspase 3 activity assay or anti-PARP. The skilled person will chose the suitable method depending on the parameter which should be analysed and depending on the advantages and limitations of each method.

E.g., when using flow cytometry the following features of the apoptotic cascade can be observed:
Expression of proteins involved in apoptosis
Activation of caspases
Changes in the mitochondrial membrane potential
Changes in the plasma membrane
Cell shrinkage
Chromatin changes The caspase 3 activity assay e.g. allows specific, quantitative detection of caspase 3 activity in cellular lysates after induction of apoptosis. Caspase 3 activation plays a key role in initiation of cellular events during the early apoptotic process. The immunosorbent enzyme assay principle of this kit guarantees high specificity without cross-reactions with other known caspases. The fluorochrome generated by proteolytic cleavage of the caspase substrate is proportional to the concentration of activated caspase 3 in the lysates.

The mitochondrion has a central role in apoptosis, during which the membrane potential collapses, a change which is best measured by flow cytometry (Zamzami et at, 1995). There are several dyes which are sequestered in the mitochondria (Galluzi et al., 2007). They include chloro-methyl-X rhosamine, rhodamine 123 and 3,3'-dihexyloxacarbocyanine-$DiOC_6$. When the mitochondrial membrane potential (MMP) collapses, the dye redistributes through the cytoplasm and forms a new equilibrium with the external medium, resulting in a loss of dye from the cell. Another dicyanine dye is JC-1, whose fluorescence shifts from green to red depending on the state of aggregation of the dye so that, when the dye is concentrated in the mitochondria, it fluoresces red; on its release, it is diluted and fluoresces green. The ratio of green to red fluorescence is measured. The dye, tetramethylrhodamine, ethyl ester, perchlorate (TRME), works in a similar fashion. The fluorescence is quenched when the dye is sequestered in the mitochondria; on its release into the cytoplasm, its fluorescence increases.

In order to compare the change in the rate of apoptosis, cells with increased apoptosis one sample of cells could be treated with KdPT according to the invention and a control sample of cells remains untreated. E.g. apoptosis rate in epithelial cells might be measured by a M30-ApoptosisSense ELISA (PEVIVA, Bromma, Sweden), detecting cytokeratin 18 with a specific monoclonal M30 antibody, whereas before cytokeratin 18 was cleaved by the enzyme caspase. While the test sample is stimulated with KdPT solved in routine medium (SFM, white column), the control sample is stimulated with the routine-medium alone. The apoptosis rate of both samples can be compared at different time points after suitable incubation periods. Suitable incubation periods are e.g. in the range of about 30 min. to 3 days, or in the range of about 1 h to 2 days, or in the range of about 1 h to 30 h or about 12 to about 24 h.

A disease with increased apoptosis comprises any disease for which increased apoptosis is described in the prior art. A disease with increased apoptosis encompasses any type of disorders in which apoptosis is involved, such as, for example, autoimmune diseases, neurogenerative disorders, myocardial infarction, stroke or inflammatory diseases such as Crohn's disease.

In the context with the present invention the term "therapeutic or prophylactic therapeutic treatment" comprises prophylactic treatments such as complete prevention of occurrence of an increased apoptosis or therapeutic treatment for improvement or healing of already occurred physical change due to increased apoptosis or in order to prevent further aggravation of. disease (activity) due to increased apoptosis. As for effectiveness of the prophylactic and/therapeutic treatment, the term should be construed in its broadest sense including improvement of findings diagnosed by a doctor and improvement of rational symptoms. The term "cosmetic treatment" comprises any treatment that serves in order to improve cosmetic features e.g. due to a disease injury or that serves in order to delay naturally occurring undesired effects e.g. due to skin aging or to heal or restore such undesired effects.

Target of the treatment with KdPT or a pharmaceutically acceptable salt might generally be any kind of cells, tissues or organs that are impacted by increased apoptosis. Thus, according to a further embodiment of the invention the inventive use can be directed to the treatment of Crohn's disease, AIDS, myocardial infarction, stroke, reperfusion injury, toxin-induced liver disease or neurodegenerative disorders such as Alzheimer's disease, Parkinson's disease, amyotrophic lateral sclerosis, retinitis pimentosa or cerebellar degeneration.

The use according to the present invention might e.g. be applied in ischemia cases, e.g. after a transplantation of an organ, e.g. heart or kidney. Also in other ischemia cases such as e.g. in the context with heart diseases, transient ischemic attacks, cerebrovascular accidents, ruptured sensitive to inadequate blood supply KdPT or a pharmaceutically acceptable salt thereof can be used according to the present invention.

Apoptosis has been described in various human and animal models of ischemia-reperfusion injury, including heart, liver, kidney and lungs: Apoptosis appears to be a significant type of cell loss in human lungs after transplantation, and this may contribute to ischemia-reperfusion injury during the early phase of graft reperfusion. This cell loss might be responsible for severe organ dysfunction, which is seen in 20% of patients after lung transplantation (Fischer S. et al.: Ann Surg. 2000 Mar;231(3):424-31). Therefore, the use according to the present invention might be important for the future development of interventions to prevent cell death in transplantation.

The use of KdPT or a pharmaceutically acceptable salt thereof can also be directed to the treatment of brain ischemia and cardiac ischemia. Brain ischemia is insufficient blood flow to the brain, and can be acute (i.e., rapid) or Chronic (i.e., long-lasting). Acute ischemic stroke is a neurologic emergency that may be reversible if treated rapidly. Chronic ischemia of the brain may result in a form of dementia called vascular dementia. Cardiac ischemia may be asymptomatic or may cause chest pain, known as angina pectoris. It occurs when the heart muscle, or myocardium, receives insufficient blood flow. This most frequently results from atherosclerosis, which is the long-term accumulation of cholesterol-rich plaques in the coronary arteries. Ischemic heart disease is the most common cause of death in most western countries and a major cause of hospital admissions.

According to a further embodiment of the present invention KdPT or a pharmaceutically acceptable salt thereof is used for an anti-apoptotic treatment in diseases with increased apoptosis, wherein the anti-apoptotic effect takes place in epithelial cells. Preferred epithelial cells are e.g. cells in the intestinal epithelium, gastric epithelium, germinal epithelium, respiratory epithelium, corneal epithelium, olfactory epithelium, urothelium or endothelium. The inventive use of KdPT or a pharmaceutically acceptable salt thereof might thus also be directed to any treatment of mucous membrane disorders or dermatosis, particularly bowel diseases, gastritis, gastro-intestinal diseases, uterine diseases, respiratory diseases or diseases of the circulatory system.

According to a further embodiment of the present invention KdPT or a pharmaceutically acceptable salt thereof might also be used in order to treat bowel diseases. Both, large and small bowel can be e.g. affected by ischemia. Ischemia of the large intestine may result in an inflammatory process known as ischemic colitis. Ischemia of the small bowel is called mesenteric ischemia. Further examples of bowel disorders are, besides short-term irritations of the bowel caused by relatively mild food poisonings, also chronic bowel disorders such as Crohn's disease or ulcerative colitis.

According to a further embodiment of the present invention KdPT or a pharmaceutically acceptable salt thereof is used in order to treat mesenteric venous thrombosis in the context with coagulation disorders.

KdPT or a pharmaceutically acceptable salt thereof as described above is preferably applied in a treatment of mammalian cells particularly human cells. Embodiments of the present invention comprise e.g. the inventive use on murine cells or on human cells. A further preferred embodiment of the present invention is the inventive use of KdPT or a pharmaceutically acceptable salt thereof on human epithelial cells. Suitable target cells or target tissues include e.g.

tissues that line the inside of the mouth, the esophagus and part of the rectum which are composed of non-keratinized stratified squamous epithelium, simple squamous, columnar, or pseudostratified epithelial cells, epithelial cells line the insides of the lungs, the gastrointestinal tract, the reproductive and urinary tracts, the exocrine and endocrine glands, the outer surface of the cornea, endothelium (the inner lining of blood vessels, the heart, and lymphatic vessels) which is a specialized form of epithelium.

mesothelium, forms the walls of the pericardium, pleurae, and peritoneum.

As way of example some suitable cell lines be mentioned that might be used for the inventive treatment: humane intestinal epithelium cells such as e.g. Caco-2 cell line, or human primary intestinal endothelial cells such as HIMEC cells. Also human kidney epithel cells are suitable target cells for the inventive treatment. Also human dermal microvascular endothelial cells (HMEC) are suitable cells for the inventive treatment.

Diseases with increased apoptosis have different origins. Apoptosis can be induced by physiologic activators, damage-related inducers, therapy-associated agents or toxins.

Physiologic Activators Comprise
- molecule members of the tumor necrosis factor (TNF) family, such as the Fas ligand or TNF
- the transforming growth factor beta
- Neurotransmitters such as glutamate, dopamine, N-methyl-D-aspartate
- Growth factor withdrawal
- Loss of matrix attachment
- Calcium and
- Glucocorticoids.

Damage-Related Inducers Comprise
- Heat shock
- Viral infections
- Bacterial toxins
- Oncogenes such as myc, rel, E1A
- Tumor suppressors such as p53
- Cytolytic T-cells
- Oxidants
- Free radicals and
- Nutrient deprivation-antimetabolites.

Therapy-Associated Agents Comprise
- Chemotherapeutic drugs such as cisplatin, doxorubicin, bleomycin, cytosine, arabinoside, nitrogen mustard, methotrexate, vincristine
- Gamma radiation and
- UV radiation
- Toxins comprise e.g. ethanol and α-amyloid peptide.

Thus a further embodiment of the present invention is the use of KdPT or a pharmaceutically acceptable salt thereof for therapeutic, prophylactic therapeutic or cosmetic treatment of a disease with increased apoptosis, wherein the treatment has an anti-apoptotic effect, wherein the anti-apoptotic treatment is directed to disorders in which apoptosis is induced by physiologic activators, damage-related inducers, therapy-associated agents or toxins.

The site of action of KdPT or a pharmaceutically acceptable salt thereof might generally be located in any step of the apoptotic cascade, which are in summarize:
- Starting with receptors and ligands known to induce apoptosis,
- early initiator stages of apoptosis,
- proteins regulating and potentially inhibiting further progression of the cascade
- irreversible execution stages of the cascade, and
- the morphological events of apoptotic death.

It might, however, be advantageous if the site of action is directed to early stages of the apoptotic cascade. The inventive use of KdPT or a pharmaceutically acceptable salt can influence the extrinsic, intrinsic apoptotic pathway or to the caspase pathway.

The extrinsic pathway begins outside the cell through the activation of specific pro-apoptotic receptors on the cell surface. These are activated by specific molecules known as pro-apoptotic ligands. These ligands include Apo2L/TRAIL and CD95L/FasL and bind their cognate receptors DR4/DR5 and CD95/Fas, respectively. Unlike the intrinsic pathway, the extrinsic pathway triggers apoptosis independently of the p53 protein.

Ligand binding induces receptor clustering and recruitment of the adaptor protein Fas-associated death domain (FADD) and the initiator caspases 8 or 10 as procaspases, forming a death-inducing signaling complex (DISC). Formation of the DISC brings procaspase molecules into close proximity of one another, facilitating their autocatalytic processing and release into the cytoplasm where they activate effector caspases 3, 6, and/or 7, thereby converging on the intrinsic pathway. Dimerization may be crucial for caspase 8 activation, and clustering of the receptors and the associated DISC may enhance this activation. DISC formation is modulated by several inhibitory mechanisms, including c-FLICE inhibitory protein (c-FLIP), which exerts its effects on the DISC by interacting with FADD to block initiator caspase activation; and decoy receptors, which can block ligand binding or directly abrogate pro-apoptotic receptor stimulation. Upon DISC activation, the extrinsic pathway adopts the same effector caspase machinery as the intrinsic pathway.

It has been shown that activation of the extrinsic pathway through the binding of CD95L/FasL to CD95/Fas can result in 2 apoptotic programs, termed type I and type II. Type I cells are able to overcome the need for mitochondrial amplification of the death signal in CD95-mediated apoptosis by producing sufficient amounts of caspase 8 at the DISC to directly cleave and activate effector caspases and execute cell death. Because type I cells bypass mitochondrial involvement in CD95-mediated apoptosis, expression of Bcl-2 or Bcl-$X_L$ has no inhibitory effect on their apoptotic program. Conversely, type II cells produce minimal amounts of active caspase 8 at the DISC and require the mitochondrial amplification of the CD95 signal. This signal is probably through the pro-apoptotic BH3 domain, which only contains the Bcl-2 family member, Bid. The cleavage of Bid by caspase 8 results in its translocation to the mitochondria where it initiates the release of mitochondrial factors, which in turn augment cell death. Because type II cells rely on the apoptotic function of mitochondria, expression of Bcl-2/Bcl-$X_L$ does confer protection from CD95-mediated apoptosis (Barnhart Bcet al. *Sem Immunol.* 2003;15:185-193). An explanation for the differences between type I and type II cells remains unclear, although differential expression of inhibitors of the death receptor signaling cascade, such as c-FLIP or X-linked inhibitor of apoptosis protein (XIAP), has been suggested to play a role.

As its name suggests, the intrinsic pathway is initiated from within the cell. This is usually in response to cellular signals resulting from DNA damage, a defective cell cycle, detachment from the extracellular matrix, hypoxia, loss of cell survival factors, or other types of severe cell stress. This pathway involves the release of pro-apoptotic proteins that activate caspase enzymes from the mitochondria. This process ultimately triggers apoptosis. The intrinsic apoptotic pathway hinges on the balance of activity between pro- and anti-apoptotic members of the Bcl-2 superfamily of proteins, which act to regulate the permeability of the mitochondrial membrane (Coultas L, et al. *Semin Cancer Biol.* 2003;13: 115-123).

A further possible site of action is an intervention in the caspase-cascade. The caspase cascade plays a vital role in the induction, transduction, amplification, and execution of apoptotic signals within the cell.

The caspases are a group of intracellular cysteine enzymes that—upon activation through the intrinsic and/or extrinsic pathways—destroy essential cellular proteins, leading to controlled cell death. There are two tiers of caspase activation during apoptosis. Initiator caspases (caspases 2, 8, 9, and 10) are activated through the apoptosis-signaling pathways and activate the effector caspases (caspases 3, 6, and 7) which, in an expanding cascade, carry out apoptosis. Caspase cascades are initiated through assembly of multiprotein complexes that trigger activation of the initiator caspases, which are then released and able to activate the downstream effector caspases. Under normal conditions, caspase activity is held in check by c-FLIP and the IAP protein family, of which at least 10 have been identified, including XIAP, cIAP1, cIAP2, ILP2, MLIAP, SURVIVIN, and BRUCE. IAPs are characterized by the presence of between 1 and 3 specific domains called baculoviral repeats (BIRs), which are directly involved in their caspase-inhibitory activity. While not directly involved in apoptotic signaling per se, some of these proteins prevent cell death by suppressing endogenous initiator and effector caspase activity. Emerging evidence also suggests that IAPs may play a role in modulating cell division (Schimmer A D. *Cancer Res.* 2004;64:7183-7190). The IAPs SURVIVIN and c-IAP1 are overexpressed in several malignancies.

The present invention comprises an inventive use of KdPT or a pharmaceutically acceptable salt thereof wherein the intervention of the apoptotic cascade is directly or indirectly directed to initiator caspases or effector caspases. Initiator caspases comprise CASP2, CASP8, CASP9, and CASP10. They cleave inactive pro-forms of effector caspases, thereby activating them. Effector caspases comprise CASP3, CASP6, CASP7 which in turn cleave other protein substrates within the cell, to trigger the apoptotic process. The initiation of this cascade reaction is regulated by caspase inhibitors.

According to one embodiment of the present invention the inventive use of KdPT or a pharmaceutically acceptable salt thereof is e.g. involved in a cell change of one or more of the following target cells or processes, respectively, connected with an antiapoptotic effect: proinflammatory cytokines, cytokine receptors, inflammatory cell migration, lymphocyte proliferation, cytokine suppressors, adhesion molecules, non-cytokine proinflammatory mediators or the transcription factor NF-kB.

According to one embodiment of the present invention the inventive use of KdPT or a pharmaceutically acceptable salt thereof leads to a direct or indirect interaction with the IL-1R (interleukin-1 receptor). IL-1R is a cytokine receptor which binds interleukin 1. Two forms of the receptor exist. The type I receptor is primarily responsible for transmitting the inflammatory effects of interleukin-1 (IL-1) while type II receptors may act as a suppressor of IL-1 activity by competing for IL-1 binding. Also opposing the effects of IL-1 is the. IL-1 receptor antagonist (IL-1RA). The IL-1 receptor accessory protein (IL1RAP) is a transmembrane protein that interacts with IL-1R and is required for IL-1 signal transduction.

According to one embodiment of the present invention the inventive use of KdPT or a pharmaceutically acceptable salt thereof leads to a direct or indirect interaction with the melanocortin receptor 1.

KdPT or the pharmaceutically acceptable salts thereof might also be used as part of a composition. Thus, a further embodiment of the invention is the use of KdPT or pharmaceutically acceptable salts thereof for the manufacture of a pharmaceutical or cosmetic composition for an anti-apoptotic treatment of disorders that are related with increased apoptosis. KdPT or the pharmaceutically acceptable salts thereof can also be used to produce a medicament for the treatment and/or prevention of disorders with increased apoptosis. The embodiments indicated above are encompassed analogously by this use. KdPT or the pharmaceutically acceptable salts thereof is normally mixed with a pharmaceutically acceptable carrier or diluent. Processes known per se for producing medicaments are indicated in Forth, Henschler, Rummel (1996) Allgemeine und spezielle Pharmakologie und Toxikologie, Urban & Fischer.

Pharmaceutical compositions of the invention comprise a therapeutically effective amount of the compound of the present invention or a pharmaceutically acceptable salt thereof and can be formulated in various forms, e.g. in solid, liquid, powder, aqueous, lyophilized form. The pharmaceutical composition may be administered with a pharmaceutically acceptable carrier to a patient, as described herein. In a specific embodiment, the term "pharmaceutically acceptable" means approved by a regulatory agency or other generally recognized pharmacopoeia for use in animals, and more particularly in humans. Accordingly, the pharmaceutical composition may further comprise a pharmaceutically acceptable carrier or excipient.

Pharmaceutically acceptable carriers, which may be used in formulating the composition according the invention, comprise those described below for the composition. Other suitable pharmaceutically acceptable carriers and excipients are inter alia described in Remington's Pharmaceutical Sciences, $15^{th}$ Ed., Mack Publishing Co., New Jersey (1991) and Bauer at al, Pharmazeutische Technologie, $5^{th}$ Ed., Govi-Verlag Frankfurt (1997).

The present invention relates also to a kit for an anti-apoptotic treatment of disorders that are related with increased apoptosis comprising KdPT or pharmaceutically acceptable salt thereof and a carrier. Generally all carriers are suitable that are pharmaceutically acceptable. Generally all types of carriers are suitable for the use according to the present invention that enable a release at the desired sit of action. The person skilled in the art knows which type of carrier is suitable depending on the correspondent application form.

Carriers might be biodegrade such as Liposomes; Microspheres made of the biodegradable polymer poly(lactic-co-glycolic) acid, albumin microspheres; synthetic polymers (soluble); nanofibers, protein-DNA complexes; protein conjugates; erythrocytes virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, ethosomes, multicomposite ultrathin capsules, aquasomes, pharmacosomes, colloidosomes, niosomes, discomes, proniosomes, microspheres, microemulsions and polymeric micelles.

Polymers are the backbone of the typical transdermal drug delivery systems. Systems for transdermal delivery are, fabricated as multi-layered polymeric laminates in which a drug reservoir or a drug-polymer matrix is sandwiched between two polymeric layers: an outer impervious backing layer that prevents the loss of drug through the backing surface and an inner polymeric layer that functions as an adhesive and/or rate-controlling membrane. Transdermal drug delivery systems comprise different systems such as the reservoir systems, microreservoir systems, and the combination of reservoir and matrix-dispersion systems.

In the reservoir system, the drug reservoir is embedded between an impervious backing layer and a rate-controlling membrane. The drug releases only through the rate-controlling membrane, which can be microporous or non-porous. In the drug reservoir compartment, the drug can be in the form of a solution, suspension, or gel or dispersed in a solid polymer matrix. On the outer surface of the polymeric membrane a thin layer of drug-compatible, hypoallergenic adhesive polymer can be applied. In the Matrix systems and Drug-in-adhesive system the drug reservoir is formed by dispersing the drug in an adhesive polymer and then spreading the medicated polymer adhesive by solvent casting or by melting the adhesive (in the case of hot-melt adhesives) onto an impervious backing layer. On top of the reservoir, layers of unmedicated adhesive polymer are applied. In the Matrix-dispersion system the drug is dispersed homogeneously in a hydrophilic or lipophilic polymer matrix. This drug-containing polymer disk then is fixed onto an occlusive baseplate in a compartment fabricated from a drug-impermeable backing layer. Instead of applying the adhesive on the face of the drug reservoir, it is spread along the circumference to form a strip of adhesive rim. The drug delivery system is a combination of reservoir and matrix-dispersion systems. The drug reservoir is formed by first suspending the drug in an aqueous solution of water-soluble polymer and then dispersing the solution homogeneously in a lipophilic polymer to form thousands of unleachable, microscopic spheres of drug reservoirs. The thermodynamically unstable dispersion is stabilized quickly by immediately cross-linking the polymer in situ. Transdermal drug delivery technology represents one of the most rapidly advancing areas of novel drug delivery. This growth is catalyzed by developments in the field of polymer science. This article focuses on the polymeric materials used in transdermal delivery systems, with emphasis on the materials' physicochemical and mechanical properties, and it seeks to guide formulators in the selection of polymers. Polymers are used in transdermal delivery systems in various ways, including as matrix formers, rate-controlling membranes, pressure-sensitive adhesives (PSAs), backing layers or release liners.

Polymers used in transdermal delivery systems should have biocompatibility and chemical compatibility with the drug and other components of the system such as penetration enhancers and PSAs. They also should provide consistent, effective delivery of a drug throughout the product's intended shelf life or delivery period and have generally-recognized-as-safe status.

Depending on the correspondent need the skilled person will choose the suitable carrier in order to apply KdPT or pharmaceutically acceptable salt according to the present invention. E.g. carriers in the context with e.g. a rectal application are e.g. multi matrix systems using methacrylic acid copolymers.

If e.g. the desired site of action is the colon and KdPT or a pharmaceutically acceptable salt thereof is applied orally the carrier has to be resistant to gastric acid in order to enable a release of KdPT or the pharmaceutically acceptable salt thereof in the colon. Suitable carriers might e.g. be The administration of KdPT or pharmaceutically acceptable salts thereof or the pharmaceutical composition comprising KdPT or pharmaceutically acceptable salts thereof can be done in a variety of ways, including, but not limited to, topically, transdermally, subcutaneously, intravenously, intraperitoneally, intramuscularly or intraocularly. Preferably the pharmaceutical composition is to be administered intraperitoneally, rectally, orally or topically.

The exact dose will depend on the purpose of the treatment (e.g. remission maintenance vs. acute flare of disease), and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art. A typical dose can be, for example, in the range of 0.0001 to 100 µg kg body weight; however, doses below or above this exemplary range are envisioned, especially considering the aforementioned factors. The dose of the active compound is normally between concentrations of 1 nM and 1 mM, preferably between 1 µM and 100 µM.

A suitable administration lies e.g. in the range of 0.1-500 Pg/kg, particularly about 0.5-300 Pg/kg, or particularly about 1-100 Pg/kg or particularly about 5-70 Pg/kg or about 10-30 Pg/kg of body weight. E.g. in case of ordinary topical administration, the dose of the active compound may be in the range of 1 ng to 1 µg per $cm^2$ skin per day or in several portions daily.

The pharmaceutical composition according to the invention may be in solid, liquid or gaseous form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for topical or oral administration.

Rectal applications can be compounded in many forms. Liquid rectal medicine solutions are given by enema. Creams, lotions and ointments are applied externally or inserted internally using an applicator. Suppositories might be prepared by mixing medicine with a wax-like substance to form a semi-solid, bullet-shaped form that will melt after insertion into the rectum. Intraperitoneal injection or IP injection is the injection of a substance into the peritoneum (body cavity). In humans, the method is used to administer chemotherapy drugs to treat some cancers. A further form of administration of an inventive composition is the topic administration, for instance in form of an ointment or cream. Such an ointment or cream may additionally comprise conventional ingredients, like carriers or excipients as described above. Accordingly, a further embodiment the invention is directed to the use of a cosmetic composition comprising a compound of the invention as the active compound and a cosmetically acceptable carrier or excipient. Use of the Tripeptide KdPT or pharmaceutically acceptable salts thereof for cosmetic treatment of disorders related with increased apoptosis such as e.g. undesired aging phenomena.

KdPT or the pharmaceutically acceptable salts thereof can also be used in sprays, for example for inhalation for the treatment of disorders of the airways or the circulatory system. KdPT or the pharmaceutically acceptable salts thereof may also be added to foods. The concentration in foods may then be about 1 µM to 1 mM. It is also possible according to the invention to use KdPT or the pharmaceutically acceptable salts thereof as non-pharmaceutical addition in cosmetics. For example, creams comprising a compound of the formula (I) can be employed for irritated skin or after sunbathing.

The present invention is also related to a Kit for an anti-apoptotic treatment of diseases with increased apoptosis comprising KdPT or pharmaceutically acceptable salts thereof and a carrier. The inventive Kit might be a Kit of two or more parts and might be prepared for use in order to apply the kit in order to treat a disease with increased apoptosis in order to decrease the increased apoptosis rate.

A better understanding of the present invention and of its advantages will be had from the following examples, offered for illustrative purposes only. The examples are not intended to limit the scope of the present invention in any way.

A brief description of the drawings in accordance with the examples follows.

EXAMPLES

1. Quantitative Determination of the Apoptosis Rate in Intestinal Epithelial Cells The apoptosis rate in epithelial cells was measured by the M30-ApoptosisSense ELISA (PEVIVA, Bromma, Sweden), detecting cytokeratin 18 with a specific monoclonal M30 antibody, whereas before cytokeratin 18 was cleaved by the enzyme caspase. The caco-2 cells (human intestinal epithelial cells) grew semiconfluent in cell culture flasks, before plating them on a 6 well plate. One plate was stimulated with $10^{-5}$ and $10^{-6}$ M KdPT solved in routine medium (SFM, white column), the control plate was stimulated with the routine-medium alone. After 24 h incubation the caco-2 cells of the control plate showed a significant increase of apoptosis rate. Caco-2-cells costimulated with KdPT showed a 251% ±5.5 and 261% ±1.3 reduced rate of apoptosis (p<0.05). This result was confirmed in four independent measurements.

Figure 1:
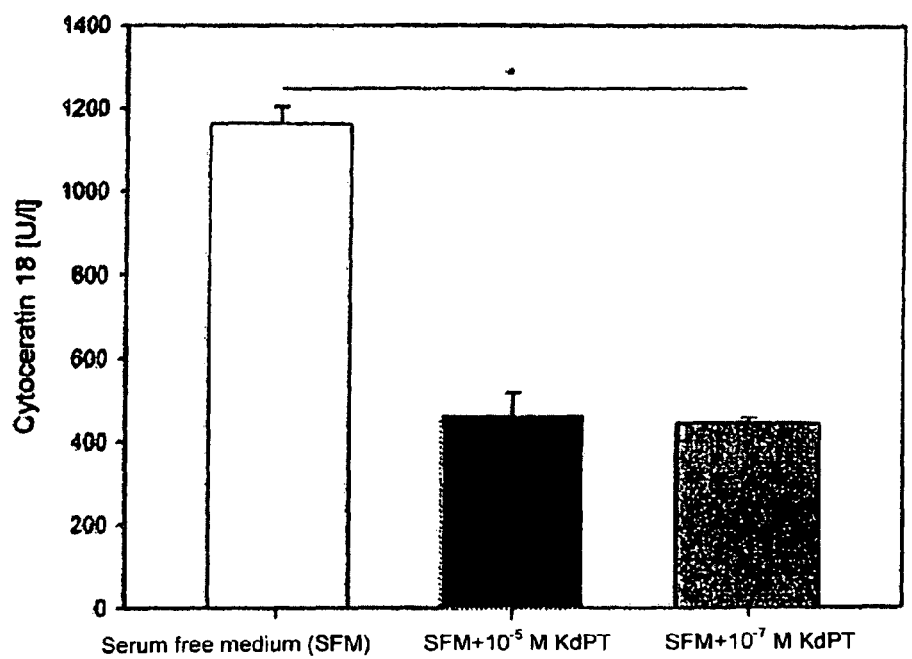
FIG. 1 is a graph showing amounts of cytokeratin 18 in unstimulated and KdPT-stimulated caco-2 cells (human intestinal epithelial cells), reflecting relative rates of apoptosis in the cells.

The costimulation with KdPT leads to a significant reduction of the apoptosis rate in human intestinal epithlial cells (Caco-2 cells) (*:p<0.05) (see FIG. 1).

Figure 2:
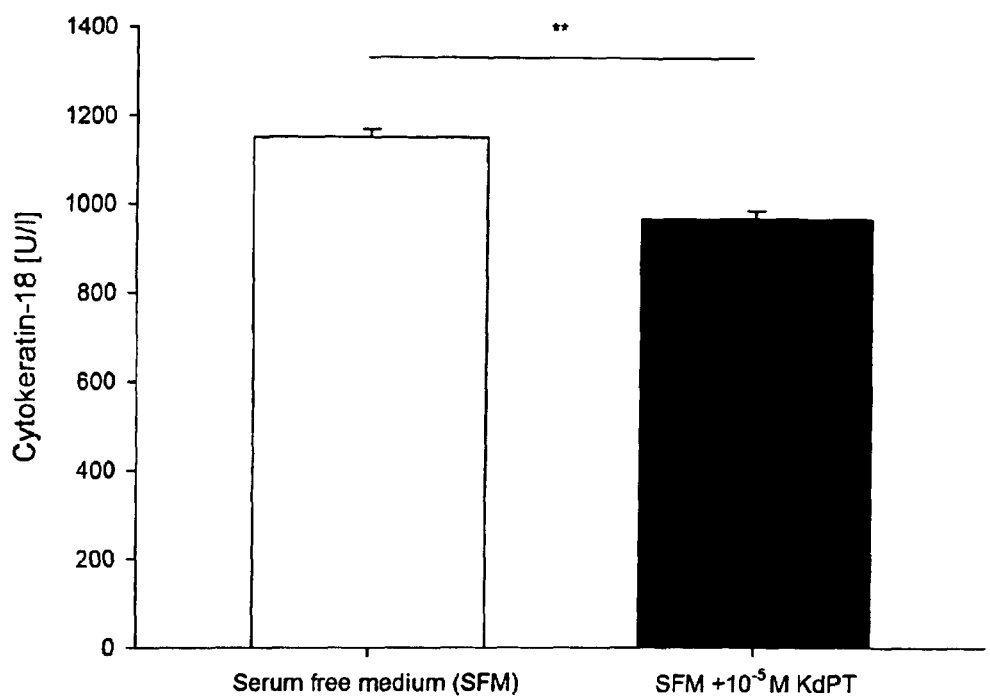
FIG. 2 is a graph showing amounts of cytokeratin 18 in unstimulated and KdPT-stimulated human dermal microvascular endothelial cells (HMEC), reflecting relative rates of apoptosis in the cells.

2. Quantitative Determination of the Apoptosis Rate in Human Dermal Microvascular Endothelial Cells (HMEC) (see FIG. 2).

The costimulation with KdPT leads to a significant reduction of the apoptosis rate in human dermal microvascular endothelial cells (HMEC).

To further elucidate the impact of KdPT administration on apoptosis in a different human cell line, additional experiments were performed in human dermal microvascular endothelial cells (HMEC) which are endothelial cells. The apoptosis rate in epithelial cells was measured by the M30-ApoptosisSense ELISA (PEVIVA, Bromma, Sweden), detecting cytokeratin 18 with a specific monoclonal M30 antibody, whereas before cytokeratin 18 was cleaved by the enzyme caspase. The HMEC cells grew semiconfluent in cell culture flasks, before plating them on a 6 well plate. One plate was stimulated with 10-5 and 10-6 M KdPT solved in routine medium (SFM, white column), the control plate was stimulated with the routine-medium alone. After 24 h incubation the caco-2 cells of the control plate showed a significant increase of apoptosis rate (1150.5 U/l +/−18.5). HMEC cells costimulated with KdPT showed a significant reduction of apoptosis rate of 19.2% (965.9 U/l +/−18.9; p=0.002). This result was confirmed in four independent measurements.

The costimulation with KdPT leads to a significant reduction of the apoptosis rate in human dermal endothelial cells (HMEC) (*:p=0.002).

3. Impact of KdPT Treatment on Epithelial Apoptosis Rate in Murine DSS-Colitis

To further evaluate the impact of KdPT on the epithelial apoptosis rate in vivo, the murine DSS colitis was performed. Dextran sodium sulfate (DSS)-induced colitis was accomplished as described in Bettenworth Am J Pathol 2011. WT mice were given 3% DSS (ICN Biomedicals Inc., Eschwege, Germany) in drinking water for 5 days, and disease activity was monitored daily by body weight measurement. Afterwards, the mice received regular drinking water again to monitor the improvement in inflammation. PBS-diluted KdPT (10 µg/day/animal; Bachem Americas Inc., Torrance, Calif.) was given daily by intraperitoneal (i.p.). injection until the end of the experiment. Control mice received PBS only.

At the end of the experiment, the mice were sacrificed and the colons removed. The colons were opened, embedded in Tissue-Tek O.C.T. (Sukura Finetek Europe, Zoeterwoude, The Netherlands), and kept frozen at −80° C. until further use. Sections (5 µm) were stained for anti-active Caspase 3 antibody (Bachem, Americas Inc., Torrance, Calif.) as a marker for apoptosis. DAPI was used for nuclear counterstaining. Immunhistological stainings were analyzed by two blinded investigators.

To assess apoptosis rate, the number of anti-active Caspase 3 positive cells per total crypt epithelial cells was counted. The number of anti-active Caspase 3 positive cells in colonic tissue was assessed as a proliferative cell marker, determined after KdPT administration in DSS-treated mice.

KdPT given i.p. dramatically decreased the number of anti-active Caspase 3 positive cells compared with control (P<0.05) reflecting a significantly reduced apoptosis rate in the epithelium of KdPT treated mice.

The invention claimed is:

1. A method for therapeutic treatment of a disease with increased apoptosis, comprising administering to a subject in need thereof a composition comprising a tripeptide (l)Lys-(d)Pro-(l)Thr (KdPT) or a pharmaceutically acceptable salt thereof in an amount in the range of 0.1-500 pg/kg of body weight of the subject, wherein administering provides an anti-apoptotic effect, and wherein the disease is selected from the group consisting of bowel diseases, gastritis and gastrointestinal diseases.

2. The method according to claim 1, wherein the anti-apoptotic effect takes place in epithelial cells.

3. The method according to claim 1 wherein the composition is administered to mammalian cells.

4. The method according to claim 1, wherein the disease in which apoptosis is induced by
 Physiologic activators,
 Damage-related inducers,
 Therapy-associated agents or
 Toxins.

5. The method according to claim 1 wherein the tripeptide KdPT or a pharmaceutically acceptable salt thereof is chemically modified.

6. The method according to claim 1, wherein the tripeptide KdPT or pharmaceutically acceptable salts thereof is administered topically, intraperitoneally, intravenously, rectally or orally.

7. The method of claim 2 wherein the epithelial cells are selected from the group consisting of intestinal epithelium and gastric epithelium.

8. The method of claim 3 wherein the mammalian cells are human cells.

9. The method of claim 1 wherein the bowel disease is Crohn's disease.

10. The method of claim 1 wherein the bowel disease is ulcerative colitis.

* * * * *